US008362306B2

(12) United States Patent
Wheeler et al.

(10) Patent No.: US 8,362,306 B2
(45) Date of Patent: Jan. 29, 2013

(54) ENERGY DENSIFICATION OF BIOMASS-DERIVED ORGANIC ACIDS

(75) Inventors: M. Clayton Wheeler, Orono, ME (US); G. Peter van Walsum, Orono, ME (US); Thomas J. Schwartz, Amesbury, MA (US); Adriaan van Heiningen, Orono, ME (US)

(73) Assignee: University of Maine System Board of Trustees, Bangor, ME (US)

( * ) Notice: Subject to any disclaimer, the term of this patent is extended or adjusted under 35 U.S.C. 154(b) by 90 days.

(21) Appl. No.: 12/912,387

(22) Filed: Oct. 26, 2010

(65) Prior Publication Data
US 2011/0098503 A1 Apr. 28, 2011

Related U.S. Application Data

(60) Provisional application No. 61/254,775, filed on Oct. 26, 2009, provisional application No. 61/258,256, filed on Nov. 5, 2009, provisional application No. 61/302,247, filed on Feb. 8, 2010.

(51) Int. Cl.
*C07C 1/00* (2006.01)
(52) U.S. Cl. ............................ 585/240; 44/605; 549/326
(58) Field of Classification Search .................. 585/240, 585/242; 549/326; 562/515; 44/605
See application file for complete search history.

(56) References Cited

U.S. PATENT DOCUMENTS

| | | | |
|---|---|---|---|
| 2,363,513 A | 11/1944 | Farrington et al. | |
| 2,794,838 A | 6/1957 | Mora | |
| 3,296,064 A | 1/1967 | Cann | |
| 3,518,170 A | 6/1970 | Koretzky | |
| 5,411,714 A | 5/1995 | Wu et al. | |
| 5,608,105 A * | 3/1997 | Fitzpatrick | 562/515 |
| 5,865,898 A * | 2/1999 | Holtzapple et al. | 127/37 |
| 5,883,266 A * | 3/1999 | Elliott et al. | 549/273 |
| 5,969,189 A | 10/1999 | Holtzapple et al. | |
| 6,043,392 A * | 3/2000 | Holtzapple et al. | 562/513 |
| 6,054,611 A | 4/2000 | Farone et al. | |
| 7,585,652 B2 * | 9/2009 | Foody et al. | 435/163 |
| 7,670,813 B2 * | 3/2010 | Foody et al. | 435/105 |
| 8,148,553 B2 * | 4/2012 | Dumesic et al. | 549/326 |
| 8,153,850 B2 * | 4/2012 | Hall et al. | 585/240 |
| 2009/0139134 A1 | 6/2009 | Yoshikuni et al. | |
| 2010/0312006 A1 | 12/2010 | Lake et al. | |

OTHER PUBLICATIONS

Breaking the Chemical and Engineering Barriers to Lignocellulosic Biofuels Next Generation Hydrocarbon biorefineries, Workshop, Washington DC, Jun. 25-26, 2007, George Huber.*
1st Brazil—U.S. Biofuels Short Course, Biomass derived furanic compounds for the production of fuels and chemical intermediates, Yuriy Roman-Leshkov, California Institute of Technology Aug. 4, 2009.*
PCT/US2010/54088 International Search Report and the Written Opinion, dated Dec. 17, 2010.
Albertazzi et al., Hydrogenation of naphthalene on noble-metal-containing mesoporous MCM-41 aluminosilicates, Journal of Molecular Catalysis A: Chemical 200, 2003, pp. 261-270.
Ardagh et al., Distillation of Acetate of Lime, Industrial and Engineering Chemistry, 1924, vol. 16, No. 11, pp. 1133-1139.
Bozell et al., Production of levulinic acid and use as a platform chemical for derived products, Resources, Conservation and Recycling 28, 2000, pp. 227-239.

(Continued)

*Primary Examiner* — Nina Bhat
(74) *Attorney, Agent, or Firm* — Choate, Hall & Stewart, LLP

(57) ABSTRACT

A process for upgrading an organic acid includes neutralizing the organic acid to form a salt and thermally decomposing the resulting salt to form an energy densified product. In certain embodiments, the organic acid is levulinic acid. The process may further include upgrading the energy densified product by conversion to alcohol and subsequent dehydration.

12 Claims, 1 Drawing Sheet

OTHER PUBLICATIONS

Chang et al., Kinetics of Levulinic Acid Formation from Glucose Decomposition at High Temperature, Chinese J. Chem. Eng., 14(5), 2006, pp. 708-712.

Davis et al., Studies of Thermal Decarboxylation of Iron Carboxylates. I. Preparation of Symmetrical Aliphatic Ketones, contribution from the Dept. of Chem., University of Maine, vol. 27, 1962, pp. 854-857.

Du et al., The chemistry of selective ring-opening catalysts, Applied Catalysis A: General 294, 2005, pp. 1-21.

Girisuta et al., Green chemicals—A Kinetic Study on the Conversion of Glucose to Levulinic Acid, Chemical Engineering Research and Design, 84(A5), 2006, pp. 339-349.

Girisuta et al., Kinetic Study on the Acid-Catalyzed Hydrolysis of Cellulose to Levulinic Acid, Ind. Eng. Chem. Res., vol. 46, No. 6, 2007, pp. 1696-1708.

Hayes et al., The Biofine Process: Production of Levulinic Acid, Furfural and Formic Acid from Lignocellulosic Feedstocks, Wiley-VCH Verlag GmbH & Co. KGaA, vol. 1, 2006, pp. 1-21.

Lee et al., The Mechanism of the Ketonic Pyrolysis of Calcium Carboxylates, contribution from the Dept. of Chem., University of Saskatchewan, 1953, pp. 1079-1086.

McVicker et al., Selective Ring Opening of Naphthenic Molecules, Journal of Catalysis 210, 2002, pp. 137-148.

Rand et al., Reactions Catalyzed by Potassium Fluoride. II. The Conversion of Adipic Acid to Cyclopentanone, Department of Chemistry, University of Detroit, vol. 27, 1961, pp. 1034-1035.

Renz, Ketonization of Carboxylic Acids by Decarboxylation: Mechanism and Scope, Eur. J. Org. Chem, 2005, pp. 979-988.

Resasco et al., Molecular Engineering Approach in the Selection of Catalytic Strategies for Upgrading of Biofuels, American Institute of Chemical Engineers, vol. 55, No. 5, 2009, pp. 1082-1089.

Santana et al., Evaluation of diffeent reaction strategies for the improvement of cetane number in diesel fuels, Fuel 85, 2006, pp. 643-656.

Santikunaporn et al., Ring opening of decalin and tetralin on HY and Pt/HY zeolite catalysts, Journal of Catalysts 228, 2004, pp. 100-113.

Schwartz et al., Energy densification of levulinic acid by thermal deoxygenation, Green Chemistry, 12, 2010, pp. 1353-1356.

Serrano-Ruiz et al., Catalytic upégrading of levulinic acid to 5-nonanone, Green Chemistry, 12, 2010, pp. 574-577.

Solladié-Cavallo et al., Heterogeneous hydrogenation of substituted phenols over Al2O3 supported ruthenium, Journal of Molecular Catalysis A: Chemical 273, 2007, pp. 92-98.

Squibb, M.D., Improvement in the Manufacture of Acetone, 1895, pp. 187-201.

Tailleur et al., The effect of aromatics on paraffin mild hydrocracking reactions (WNiPd/CeY-Al2O3), Fuel Processing Technology 89, 2008, pp. 808-818.

Valor et al., Thermal decomposition of the calcium salts of several carboxylic acids, Thermochimica Acta 389, 2002, pp. 133-139.

Von L. Ruzieka et al., Ruzicka, Carbon rings. XX. Unsaturated 16- and 18-membered rings of the civetone type, Helevetica chimica acta, vol. 15, 1932, pp. 1459-1467.

Yang et al., Thermal Degradation Kinetics of Calcium-Enriched Bio-oil, AIchE Journal, vol. 54, No. 7, 2008, pp. 1945-1953.

Chapter XXIII. Production of Acetone by Means Other Than Fermentation, http://chestofbooks.com/science/chemistry/Distillation-Principles-and-Processes/Chapter . . . , 2010, pp. 1-6.

Biomass derived Furanic compounds or the production of fuels and chemical intermeidaries, Aug. 4, 2009.

Barriers to Lignocellulosic Biofuels, Online Publication, Mar. 2008.

* cited by examiner

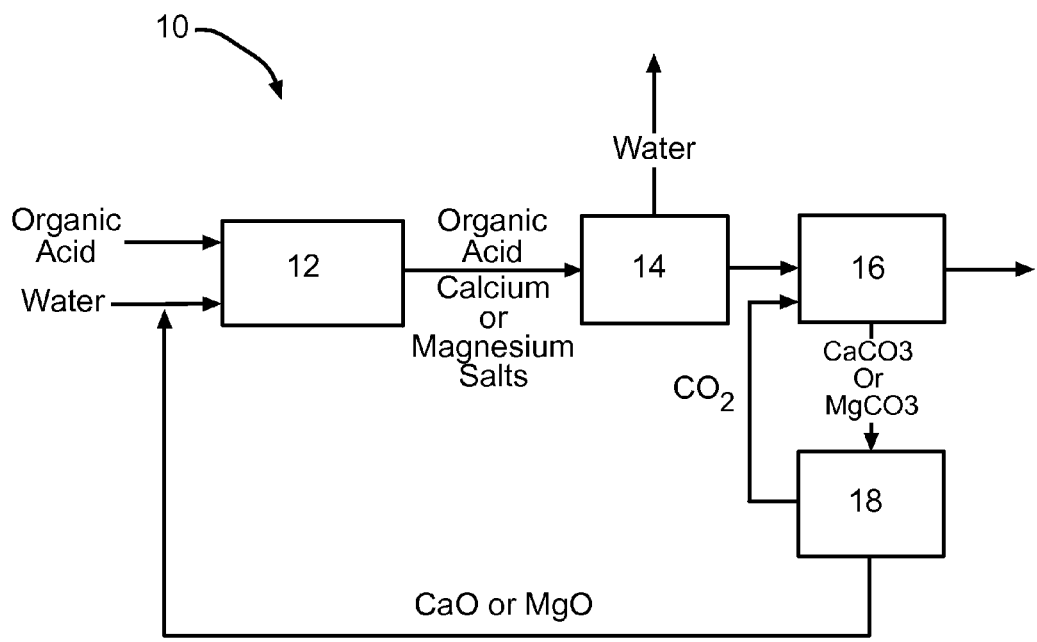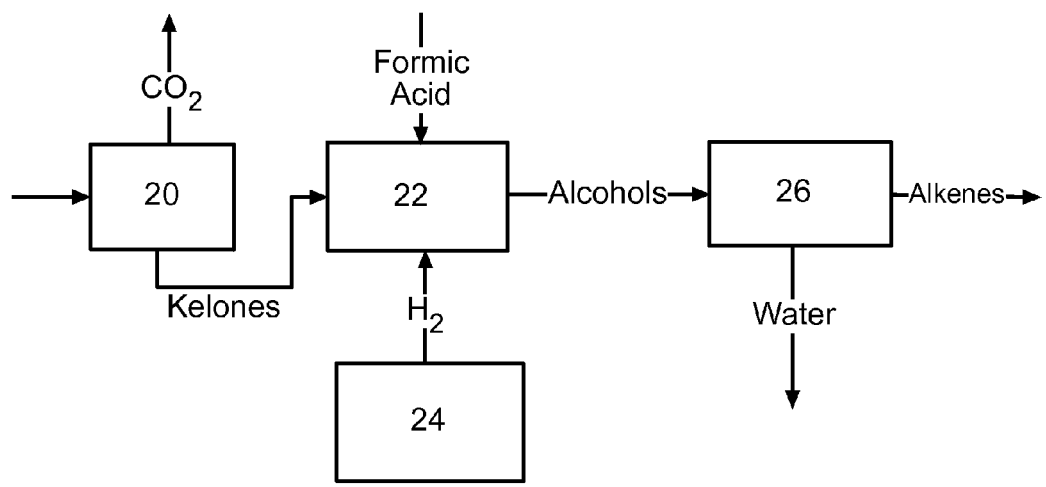

US 8,362,306 B2

ENERGY DENSIFICATION OF BIOMASS-DERIVED ORGANIC ACIDS

CROSS-REFERENCE TO RELATED APPLICATIONS

This application claims the benefit of U.S. Provisional Application No. 61/254,775, filed Oct. 26, 2009, No. 61/258,256, filed Nov. 5, 2009, and No. 61/302,247, filed Feb. 8, 2010, the disclosures of which are incorporated herein by reference.

This invention was made with government support under DE-FG02-07ER46373 awarded by the Department of Energy, Office of Experimental Program to Stimulate Competitive Research and DE-FG02-08G018165 awarded by the Department of Energy. The U.S. Government has certain rights in the invention.

BACKGROUND OF THE INVENTION

This invention relates in general to the production of useful products from biomass, and in particular to the energy densification of biomass-derived organic acids to produce products suitable for high energy density fuels.

World oil production is forecasted to peak within the next five years, which implies it is likely that the price of oil will increase significantly in the future. This is also evidenced by the fact that the price of oil was back to about $80/bbl at the end of 2009 after the worst economic recession since World War II. Furthermore, the combustion of fossil fuels is considered to be the major factor responsible for trends in global climate change, equaling about 82% of net green house gas emissions. In order to address these problems, there is a pressing need for the development of renewable fuels and energy derived from biomass, wind, geothermal heat and solar radiation in order to meet future economic and environmental requirements. Among these renewable resources, biomass is considered to be the only sustainable and carbon-neutral source for the production of liquid fuels. The US has the potential to sustainably produce biomass which can replace more than one-third of the 2004 US petroleum consumption.

Levulinic acid has been identified as one of the top value added, biomass-derived chemicals by the U.S. Department of Energy, and it can be produced from cellulose-containing biomass in high yields using the "Biofine" process. Levulinic acid esters such as ethyl levulinate have low energy content (26 MJ kg-1) compared to petroleum based fuels (46 MJ kg-1). While this relatively low energy density might be acceptable for ground transportation fuels it is unacceptable for aviation fuels. The energy density of the fuel impacts both the range and the carrying capacity of the aircraft. Therefore, it would be desirable to provide a process for the energy densification of biomass-derived levulinic acid and other organic acids.

SUMMARY OF THE INVENTION

A process for upgrading an organic acid includes neutralizing the organic acid to form a salt and thermally decomposing the resulting salt to form an energy densified product. In certain embodiments, the organic acid is levulinic acid. The process may further include upgrading the energy densified product by conversion to alcohol and subsequent dehydration.

BRIEF DESCRIPTION OF THE DRAWINGS

FIG. 1 is a schematic drawing of a process for energy densification of biomass-derived organic acids according to the invention.

DETAILED DESCRIPTION OF THE PREFERRED EMBODIMENT

A process is provided for upgrading organic acids to form energy densified products. In certain embodiments, the process is a pathway for converting biomass-derived organic acids to higher molecular weight ketones, alcohols and hydrocarbons. The higher molecular weight hydrocarbons can have high energy density and properties suitable for diesel and jet fuels.

This description focuses on conversion of levulinic acid, but the process could be extended to any feedstock that has a high fraction of organic acids or esters, pyrolysis oils for instance.

FIG. 1 shows an embodiment of the process 10 for energy densification of biomass-derived organic acids. The process includes a neutralization reactor 12 for acid neutralization and salt formation. Addition of calcium oxide, a chemical already found in Kraft pulp mills, or magnesium oxide, available in magnesium-based sulfite pulp mills, to an organic acid such as levulinic acid forms an organic acid salt, in this case calcium levulinate. The organic acid calcium salts flow to a dryer 14 for the removal of water. This salt can be thermally decomposed at temperatures between 200 and 800° C. in a furnace 16. The partially-deoxygenated compounds formed during the decomposition reaction are predicted to have Higher Heating Values (HHVs) comparable to diesel and #2 fuel oils (above 35 MJ/kg). As a comparison, the HHV of levulinic acid is 21 MJ/kg, and those of wood-derived pyrolysis oils are about 25 MJ/kg. The calcium carbonate or magnesium carbonate formed in the decomposition reaction flows to a kiln 18, where it is converted to calcium oxide or magnesium oxide and carbon dioxide. The calcium oxide or magnesium oxide can be recycled to the beginning of the process.

The HHVs of the organic acid salt decomposition products can be improved by further processing. In the illustrated process, the decomposition products are condensed in a condenser 20. The decomposition products with ketone functionalities can then be hydrogenated in a hydrogenation reactor 22, using catalysts such as Raney nickel or Ru, Pd, Pt on supports such as activated carbon, silica or alumina to form alcohols. Biomass gasification or water electrolysis 24 can be used to provide hydrogen to the hydrogenation reactor 22. The alcohols from the hydrogenation reactor 22, along with decomposition products containing alcohol functionalities can then be dehydrated in a dehydration reactor 26 using catalysts, such as alumina, supported metals, or ion exchange resins, to form mixtures of aliphatic and aromatic hydrocarbons.

Formation of the organic acid salts may also be done using magnesium oxide or any other suitable material capable of neutralizing the organic acid to form a salt, including any suitable inorganic salt. Magnesium carbonate is known to calcine at lower temperatures than calcium carbonate. Consequently, potential energy savings exist if magnesium oxide is utilized in the process in place of calcium oxide.

The process can be performed using any suitable equipment, such as the equipment shown in FIG. 1 or other equipment for performing the required reactions and processes. In certain embodiments, the process includes a pyrolysis reactor system for the thermal decomposition reaction, and the pyrolysis reactor system uses a heat transfer medium such as sand or steel shot.

All of these processes could be integrated into existing infrastructure in a Kraft pulp mill. For example, the process could be integrated by making use of existing permits, infrastructure, process chemicals and/or equipment (such as the lime cycle).

The hydrogen used in the process can be provided by any suitable source. The current process generates unsaturated hydrocarbons, reducing hydrogen feed requirements because current methods for deoxygenation of unsaturated oxygenates result in saturation of the hydrocarbon products. Using emerging technology, it is possible to generate the required hydrogen from formic acid which is a byproduct of levulinic acid formation. The hydrogen from formic acid can also be transferred to the products catalytically which would eliminate the need for hydrogen generation. Another emerging technology allows the electrolysis of water using sunlight as an energy source. If water removed in the dehydration step can be split to re-form the hydrogen needed for hydrogenation the net consumption of hydrogen effectively drops to zero. Another option utilizes synthesis gas produced from the gasification of the kraft pulping liquor (black liquor).

In brief, the above-described process can be used for upgrading of mixtures containing organic acids by neutralizing with calcium hydroxide or magnesium hydroxide and thermally decomposing the resulting salt to form energy-dense products. In certain embodiments, the process further includes upgrading the energy-dense products by conversion to alcohols and subsequent dehydration.

In a particular embodiment, the process provides a pathway for converting C6 sugars to C9 ketones, alcohols and hydrocarbons. The longer-chain hydrocarbons can have high energy density and properties suitable for diesel and jet fuels.

The process focuses on a synthesis route to form longer chain unsaturated hydrocarbons that involves the combination of two levulinic acid molecules. Addition of calcium oxide or magnesium oxide, to levulinic acid forms an organic salt, calcium levulinate or magnesium levulinate, respectively. These salts can be thermally decomposed to form a 9-carbon tri-ketone. The oxygen:carbon ratio of this compound is 1:3. Additionally, this compound can be hydrogenated, using catalysts such as Raney nickel or Ru on activated carbon, and dehydrated using acid catalysts, such as alumina, to form nonene, an unsaturated linear chain hydrocarbon that would be an energy-dense substitute for petroleum diesel and could be further alkylated to branched hydrocarbons suitable for jet fuels.

In brief, this embodiment of the process can be used for dimerization of levulinic acid into a novel 9-carbon tri-ketone using either a calcium or magnesium salt of levulinic acid. The IUPAC name for this tri-ketone is Nonane-2,4,8-one. The process may further include the catalytic hydrogenation of this ketone into a 9-carbon tri-ol. The IUPAC name for this tri-ol is Nonane-2,4,8-ol. The process may further include the catalytic dehydration of this tri-ol to form 2,4,6-Nonene to be used as a diesel fuel, biomass-derived jet fuel replacement, or alkylation feedstock to create larger, branched hydrocarbons.

The above-described process for upgrading organic acids to form energy densified products can be called a "thermal deoxygenation" (TDO) process in certain embodiments, and it can be described in more detail as follows. The process for thermal deoxygenation can be used to upgrade levulinic acid whereby levulinic acid is neutralized with calcium hydroxide, and the resulting salt is heated to between 200° C. and 800° C. The products are cyclic and aromatic and have low oxygen to carbon ratios, improved energy density, and may be candidates for upgrading to hydrocarbon fuels. The process may be useful for converting biomass-derived levulinic acid in an integrated forest products complex based on a kraft pulp mill which uses a lime cycle to regenerate calcium hydroxide.

Organic acids other than levulinic can be derived from biomass and may also be suitable for upgrading via TDO. Many of the top value added chemicals that can be produced from biomass are organic acids. Many of these acids have unique functionalities such as di-acid groups, alcohol groups, or carbonyl groups. We show that additional functionality leads to more complex reaction mechanisms which include aldol condensation and dehydration. When coupled with these other base-catalysed reactions we refer to the process as thermal deoxygenation (TDO) because of the significant loss of oxygen that can occur.

We find that TDO of levulinic acid results in formation of cyclic and aromatic molecules with very low oxygen to carbon ratios. The kinetics of the TDO of levulinic acid are reported below. Both the composition and physical properties of the products of TDO were characterized and the broad product distribution may facilitate upgrading to hydrocarbon fuels with a potential emphasis on aviation turbine fuels.

Calcium levulinate decomposition was studied by thermogravimetric analysis and compared to that of calcium acetate, an aliphatic organic acid. Calcium acetate is known to decompose to acetone with nearly 100% yield (reaction 1) around 400° C., and the mass loss at 700° C. is consistent with reaction 2.

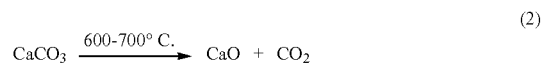

We might have expected that calcium levulinate would undergo ketonization by the following mechanism:

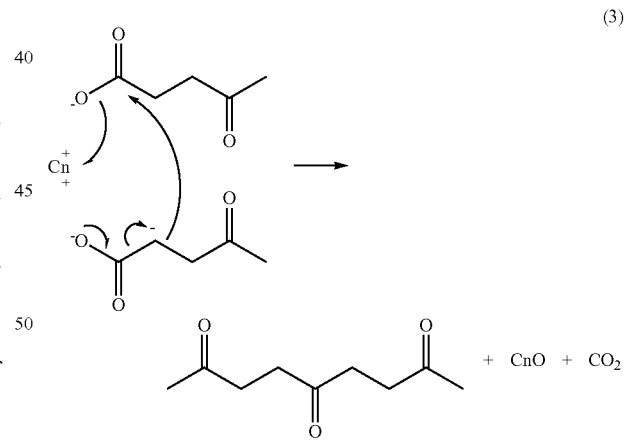

However, the TGA of calcium levulinate shows that decomposition occurs at temperatures ranging from 200-600° C. This is much broader than calcium acetate, and suggests a more complicated reaction. The residual mass at 600° C. is not consistent with the formation of calcium carbonate as would be expected based on the TGA of calcium acetate. 11% of the mass of hydrated calcium levulinate is lost as water below 200° C. Taking this into consideration, 37% of the anhydrous calcium levulinate is volatilized in the TGA. Calcium carbonate consists of an additional 37% of the mass of calcium levulinate. Thus, a further 26% by mass of the calcium levulinate remains in the residue. Total carbon analysis was performed on the char formed in the TGA at 600° C., and the results indicated that 48% of the residue is carbon (organic or inorganic), consistent with formation of a carbonaceous char in addition to calcium carbonate. While the formation of char implies a decrease in energy efficiency of the TDO reaction itself, combustion of the char can provide energy required to regenerate calcium oxide from calcium carbonate in a lime kiln. It is also probable that char formation can be reduced by appropriate reactor design to improve mass transfer of the products out of the solid mass.

The rate of decomposition vs. temperature in the TGA between 200 and 600° C. indicates the existence of at least two reaction regimes. By calculating fractional conversion from the mass loss in the TGA, a kinetic analysis was performed using the distributed activation energy model (DAEM) presented in the electronic supplementary information.

GC/MS analysis of the products formed at both 350° C. and 450° C. is consistent with the NMR analysis. No long-chain, linear molecules were identified. Rather, the analysis revealed a variety of cyclic and aromatic compounds. FIG. 2 shows a comparison of two chromatograms, one for 350° C. and one for 450° C., with the major peaks identified.

The two temperature regimes explored have different product distributions. At the lower temperature, the majority of the identified products are substituted cyclopentenones. Formation of these products is consistent with intramolecular aldol condensation and dehydration within the ketone hypothesized in reaction 3 above. For example, the two most prominent products in a chromatogram can be explained Scheme 1:

Scheme 1 Possibilities for intramolecular aldol condensation and dehydration pathways resulting in molecules exhibiting significant deoxygenation.

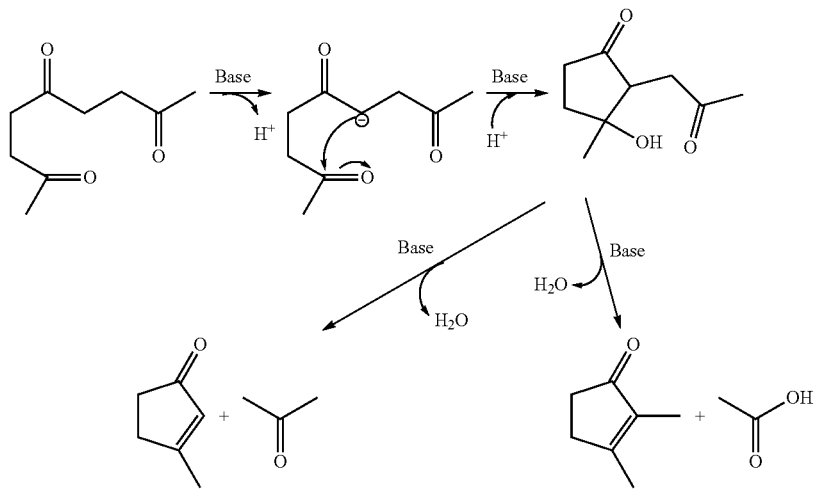

tion. The DAEM was fit using a bimodal activation energy distribution, and average activation energies were calculated as 165 kJ/mol for the reactions in the 300-400° C. range and 212 kJ/mol for the reactions in the 400-600° C. range.

Proton and carbon NMR analysis of the products of TDO are not consistent with simple ketonization of levulinic acid (reaction 3). Table 1 below presents the integration of the NMR spectra of the product of TDO at 450° C. Both proton and $^{13}C$ NMR show peaks in the range known to represent aromatic molecules. 40% of the carbon is contained in alkyl groups while 44% is contained in aromatic groups. The higher heating value of the liquid product generated at 450° C. was measured as 34.4 MJ/kg.

TABLE 1

Integration of proton and carbon NMR spectra of TDO products

| | Chemical Shift (ppm) | 13C NMR | Chemical Shift (ppm) | 1H NMR |
|---|---|---|---|---|
| Carbonyl | 215-160 | 15% | 11-8.25 | 4% |
| Aromatic/Alkene | 160-102 | 44% | 8.25-6 | 44% |
| Carbohydrate | 102-70 | 1% | 6-4.2 | 7% |
| Methoxy/Hydroxy | 70-54 | 0% | 4.2-3.51 | 0% |
| Alkyl Hydrocarbon | 54-1 | 40% | 2-0 | 45% |

The same aldol condensation and dehydration products are observed in the higher temperature chromatogram; however, there are also several higher carbon number molecules which cannot be explained by simple aldol condensation. Such molecules could be explained by a series of free-radical chain reactions which are likely to occur at high temperatures.

A mechanism for free radical formation and chain reaction has been proposed for the pyrolysis of ethylene-carbon monoxide copolymers. Ethylene-carbon monoxide copolymer has a structure which, when truncated, is identical to that of the ketone hypothesized in reaction (3). It would be possible, then, to form several small radicals which could feasibly result in the significantly deoxygenated C9-C12 aromatics found levulinic acid TDO products.

To verify the importance of the calcium in TDO, a sample of pure levulinic acid was heated to 450° C. under a nitrogen atmosphere, and the products were condensed and analyzed by GC/MS. The major peak corresponded to levulinic acid, two minor peaks were identified corresponding to 5-methyl-hydrofuran-2-ones (cyclization and dehydration products), and a fourth peak was identified as 1,2-dimethyl cyclopentane. Calcium, functioning as a base, must then facilitate the ketonic decarboxylation of levulinic acid. The resulting ketone is an intermediate in the overall reaction, and is further deoxygenated by aldol condensation and dehydration.

The energy yield of the products is estimated to be on the order of 80% of the heating value of the levulinic acid feed, and we estimate the energy efficiency that might be realized for the TDO process is on the order of 75%. The basis for calculation was production of 23% char, a product HHV of 35 MJ/kg, and minimal $CO_2$ formation. If char formation can be reduced, the energy yield could be nearly 100% with a process efficiency on the order of 85%. The process consists of four reaction steps: 1) slaking of calcium oxide, 2) neutralizing of levulinic acid, 3) thermal reaction of calcium levulinate, and 4) regeneration of calcium oxide in a lime kiln. Steps 1 and 2 are mildly exothermic, and step 3 is endothermic. Step 4 can be either exothermic or endothermic depending on the relative amount of char formed.

The pyrolytic nature of TDO promises a tolerance of varying composition and purity of a levulinic acid feedstock produced from municipal solid wastes. Furthermore, the economics of production of biofuels from calcium levulinate would be much improved when integrated within an existing industrial forest products complex such as a kraft pulp mill. Such a complex already operates a lime kiln, and has facilities for processing lignocellulosic biomass, treatment of waste water, and generation of steam and electricity from biomass.

A novel process for the thermal deoxygenation (TDO) of biomass has been presented. Functionalized organic acids such as levulinic acid can be neutralized with calcium hydroxide and then subjected to high temperatures to form significantly deoxygenated and energy densified products. We have determined kinetic parameters for the process when applied to levulinic acid and proposed a mechanism for the formation of the identified products.

To be candidates for hydrocarbon transportation fuels, the TDO products may be further upgraded. Hydrodeoxygenation of the aqueous fraction of pyrolysis oils has been accomplished by hydrogenation and dehydration using Ru and Pt catalysts. Such hydrodeoxygenation of the TDO products would likely yield a feedstock similar in properties to the naptha fraction of crude oil which could then be further refined using existing petroleum processing technologies. Ring opening and isomerization could be accomplished with noble metal catalysts on acidic supports, and resulting C7-C12 parrafins would be suitable for use as a jet fuel blending agent.

Using waste lignocellulosic biomass; it may be possible to fuel a sizable fraction of the existing US transportation fleet without vehicle modification using a bio-based hydrocarbon source. While this may seem like an optimistic claim, the US Departments of Energy and Agriculture have proposed that it is possible to replace nearly 30% of the US petroleum consumption with bio-based fuels by 2030, using approximately 1 billion dry tons of biomass feedstock per year. This capacity exists with only modest improvements to land use and no disruption to food supplies. The use of domestically available biomass as a feedstock would not only improve the energy security of the United States, it would provide a sustainable and carbon-neutral fuel which has the potential to help mitigate the effects of global climate change. Optimally such a process would be co-located at a kraft pulp mill.

Preliminary experiments of magnesium levulinate TDO have generated results similar to calcium levulinate TDO with the exception that magnesium levulinate decomposes at temperatures approximately 50° C. lower than calcium levulinate. This is advantageous because magnesium carbonate can be regenerated to magnesium oxide at lower temperatures than calcium carbonate can be regenerated to calcium oxide thus lowering energy costs for both TDO and the overall process.

EXPERIMENT 1

The feasibility of the decomposition of the calcium salt of levulinic acid was assessed using thermogravimetric analysis (TGA). Calcium levulinate, purchased from Sigma Aldrich (CAS 5743-49-7), was compared to anhydrous calcium acetate, also purchased from Sigma (CAS 114460-21-8). Experiments were conducted using a TA Instruments Q500 TGA. Approximately 5 mg samples were loaded onto platinum pans as very thin layers to minimize mass transfer limitations caused by the melting calcium levulinate salt, which forms a "a pasty, porous and spongy mass" that can trap product vapors. The TGA was performed as a 20° C./min ramp from 25° C. to 1000° C. using nitrogen (liquid N2 boil-off) as a sweep gas.

Kinetic parameters were determined using TGA coupled with the distributed activation energy model (DAEM). DAEM assumes many parallel, irreversible, first order reactions, and has been applied to both coal and biomass pyrolysis. Using TGA, the mass loss is considered to be the fractional conversion, which allows the determination of the activation energy assuming a constant frequency factor. The DAEM was fit using a bimodal activation energy distribution, and average activation energies were calculated as 165 kJ/mol for the reactions in the 300-400° C. range and 212 kJ/mol for the reactions in the 400-600° C. range.

The TDO of levulinic acid was performed using a Parr 300 mL stirred tank reactor. Calcium levulinate was prepared by neutralizing levulinic acid (Acros Organics, CAS 123-76-2) with calcium oxide (Sigma, CAS 1305-78-8) slaked in water at 50° C. for 10 minutes. The resulting salt was dried in an oven at 105° C., crushed, and screened through a number 150 USA Standard Sieve. The Parr reactor was configured to allow the flow-through of nitrogen sweep gas (industrial grade) with a liquid nitrogen condenser on the outlet. Glass beads were used to enhance heat transfer. Two different temperature regimes were characterized by ramping the reactor temperature to both 350° C. and 450° C.

The products of TDO were characterized using calorimetry for heating value, nuclear magnetic resonance (NMR) spectroscopy, and gas chromatography/mass spectrometry (GC/MS). Higher heating value was measured using a Parr Model 1241 oxygen bomb calorimeter. Chemical functional group analysis was carried out using a Varian Unity Plus 400 NMR. Samples were diluted in 1:1 volume ratio with dimethyl sulfoxide as a solvent and using tetramethylsilane as an internal standard. Functional groups were determined using a library of proton and $^{13}C$ measurements made on more than 50 compounds common in pyrolysis oils. The chemical shift regions representative of different functional groups were integrated to determine the percent of carbon which exists as each functional group.

Total carbon analysis was performed by the University of Maine Analytical Laboratory and Maine Soil Testing Service. The analysis is a combination of total organic and total inorganic carbon. Samples are combusted in an oxygen atmosphere between 1050-1350° C. Helium is used as a carrier gas to transfer the released gasses through an infrared detector to determine carbon dioxide concentration. Steel wool is used to remove excess oxygen.

The structures of prominent compounds in the products were elucidated using a Shimadzu GCMS-QP2010S equipped with a Shimadzu SHRX1-5MS column. Samples were diluted in dichloromethane and dried over sodium sulfate. This analysis was qualitative as no internal standard was used. Chemical structures were determined by comparison with several NIST libraries provided in Shimadzu's GCMS solution software. The temperature program for the GC column oven ramped from 40° C. to 120° C. at 1.5° C./min and then held at 120° C. for 10 minutes. The oven was then ramped from 120° C. to 220° C. at 5° C./min and held at 220° C. for 10 minutes. Finally, the column was ramped from 220° C. to 250° C. at 25° C./min and held at 250° C. for 10 minutes. The major compounds in the chromatogram were indentified by their mass spectra.

EXPERIMENT 2

In another experiment, the feasibility of the decomposition of the magnesium salt of levulinic acid was assessed using thermogravimetric analysis (TGA). Levulinic acid was neutralized using magnesium hydroxide to produce magnesium levulinate which was dried in an oven. Experiments were conducted using a TA Instruments Q500 TGA. Approximately 5 mg samples were loaded onto platinum pans as very thin layers.

The TDO of levulinic acid was performed using a Parr 1.8 L stirred tank reactor. Magnesium levulinate was prepared by neutralizing levulinic acid. The resulting salt was dried in an oven at 105° C., crushed, and screened through a number 150 USA Standard Sieve. The Parr reactor was configured to allow the flow-through of nitrogen sweep gas (industrial grade) with a liquid nitrogen condenser on the outlet. Stainless steel ball bearings were used to enhance heat transfer.

The structures of prominent compounds in the products were elucidated using a Shimadzu GCMS-QP2010S equipped with a Shimadzu SHRX1-5MS column. Samples were diluted in dichloromethane and dried over sodium sulfate. This analysis was qualitative as no internal standard was used. Chemical structures were determined by comparison with several NIST libraries provided in Shimadzu's GCMS solution software. The temperature program for the GC column oven ramped from 40° C. to 120° C. at 1.5° C./min and then held at 120° C. for 10 minutes. The oven was then ramped from 120° C. to 220° C. at 5° C./min and held at 220° C. for 10 minutes. Finally, the column was ramped from 220° C. to 250° C. at 25° C./min and held at 250° C. for 10 minutes. The major compounds in the chromatogram were identified by their mass spectra.

EXPERIMENT 3

In another experiment, we thermally deoxygenated unpurified (raw) levulinic acid produced from municipal solid waste by Biofine's Gorham, Maine facility. The intent of the experiment was to demonstrate that the process would be tolerant of impurities. Not only was the process robust, but some of the impurities improved the quality of the product.

Significant observations about the experiment included: 1) The products had even lower oxygen content relative to those produced from pure levulinic acid. 2) Since there were fewer ketone functionalities, most of the hydrocarbon products spontaneously separated from the aqueous phase. This is significant because it will reduce energy requirements for purification of the hydrocarbon products. 3) The higher heating value increased from 34 to 39 MJ/kg because of the decrease in oxygen content. 4) Some of the impurities that were present in the feed were identified and included: Formic acid, chlorine, sulfur, sodium, magnesium, potassium, and calcium.

The results of the experiment suggest that organic acids or inorganic salts can be added to vary the properties of the product. Ultimately, there will be an economic tradeoff between carbon conversion efficiency and hydrogen consumption in upgrading the products of this process.

What is claimed is:

1. A process for upgrading a biomass derived organic acid comprising providing an organic acid; neutralizing the organic acid to form a salt; and heating the salt to between 200° C. and 800° C. to form an energy densified product, wherein the energy densified product contains at least 34 MJ/kg of stored energy.

2. The process of claim 1 wherein the neutralization is done with a compound selected from the group consisting of calcium hydroxide, calcium oxide, calcium carbonate, magnesium oxide, magnesium carbonate and magnesium hydroxide.

3. The process of claim 1 wherein the organic acid comprises a mixture of organic acids to form energy densified products.

4. The process of claim 1 further comprising upgrading the energy densified product by conversion to alcohol and subsequent dehydration.

5. The process of claim 1 wherein the salt is heated in a pyrolysis reactor system and the pyrolysis reactor system includes a heat transfer medium.

6. The process of claim 1 wherein the organic acid includes impurities.

7. A process for upgrading levulinic acid comprising providing levulinic acid; neutralizing the levulinic acid to form a salt; and heating the salt to between 350° C. and 450° C. to form an energy densified product, wherein the energy densified product contains no more than 15% carbonyl groups.

8. The process of claim 7, wherein the neutralization is done with a compound selected from the group consisting of calcium hydroxide, calcium oxide, calcium carbonate, magnesium oxide, magnesium carbonate, and magnesium hydroxide.

9. The process of claim 7, further comprising upgrading the energy densified product by conversion to alcohol and subsequent dehydration.

10. The process of claim 7, wherein the organic acid includes impurities.

11. The process of claim 1, wherein the organic acid is levulinic acid.

12. The process of claim 1, wherein the organic acid is lactic acid.

* * * * *